(12) United States Patent
Lee et al.

(10) Patent No.: US 6,441,200 B1
(45) Date of Patent: Aug. 27, 2002

(54) METHOD FOR PREPARING DL-α-TOCOPHEROL WITH A HIGH YIELD AND HIGH PURITY

(75) Inventors: Sijoon Lee; Jeong-Soo Kim; Young-Seek Yoon; Myung-Jun Kim; Jun-Tae Choi; Byong-Sung Kwak, all of Taejon (KR)

(73) Assignee: Sk Corporation, Seoul (KR)

( * ) Notice: Subject to any disclaimer, the term of this patent is extended or adjusted under 35 U.S.C. 154(b) by 17 days.

(21) Appl. No.: 09/711,824

(22) Filed: Nov. 13, 2000

(30) Foreign Application Priority Data

Dec. 14, 1999 (KR) ............................................. 99-57483

(51) Int. Cl.$^7$ ............................................. C07D 311/72
(52) U.S. Cl. ..................................................... 549/413
(58) Field of Search ........................................ 549/413

(56) References Cited

U.S. PATENT DOCUMENTS

| | | | |
|---|---|---|---|
| 4,217,285 A | 8/1980 | Yoshino et al. | 260/345.5 |
| 4,634,781 A | 1/1987 | Finnan | 549/411 |
| 4,639,533 A | 1/1987 | Finnan | 549/411 |
| 5,663,376 A | 9/1997 | Hirose et al. | 549/411 |
| 5,886,197 A | 3/1999 | Hirose et al. | 549/411 |

*Primary Examiner*—T. A. Solola
(74) *Attorney, Agent, or Firm*—Abelman, Frayne & Schwab

(57) ABSTRACT

Disclosed is a method for preparing DL-α-tocopherol through the condensation of isophytol or phytol derivatives and trimethylhydroquinone (TMHQ) using a catalyst system comprising a divalent metal halogen compound, silica gel and/or silica-alumina, and a Brönsted acid. Isophytol or phytol derivatives are slowly added to trimethylhydroquinone for the condensation thereof at 80 to 135° C. over 30 to 60 min in the presence of the metal halogen and the silica gel and/or silica-alumina. In the presence of the Brönsted acid, the intermediates are converted into the product. The silica gel and/or silica-alumina is washed with a polar solvent for recovery. The catalyst system can remarkably reduce side-reactions upon the condensation of isophytol or phytol derivatives and TMHQ, thus producing DL-α-tocopherol with a high purity at a high yield. Also, the catalyst system can be regenerated in succession because of its being able to avoid the decrease of catalytic activity attributed to the adsorption of organic materials; thus reducing the production cost of DL-α-tocopherol and the quantity of industrial wastes generated. With these advantages, the catalyst system can be effectively used in preparing highly pure DL-α-tocopherol at a high yield on a commercial scale.

15 Claims, No Drawings

METHOD FOR PREPARING DL-α-TOCOPHEROL WITH A HIGH YIELD AND HIGH PURITY

BACKGROUND OF THE INVENTION

1. Field of the Invention

The present invention relates to a preparation method of DL-alpha-tocopherol of high purity through the condensation between isophytol or phytol derivatives and trimethylhydroquinone (TMHQ). More particularly, the present invention relates to a combined catalyst system which includes a divalent halogen compound $MX_2$ (wherein M is a divalent metal ion and X is halogen) as a main catalyst component, silica gel and/or silica-alumina as a co-catalyst and a Brönsted acid as an additional catalyst component and a regenerating component for the co-catalyst, thereby enabling the preparation of DL-α-tocopherol with a high purity at a high yield on a commercial scale.

2. Description of the Prior Art

For the past few decades, extensive effort has been made to effectively prepare DL-α-tocopherol by use of Zn(II) ions as metallic catalysts (Lewis acid catalyst). Conventionally, the DL-α-tocopherol is prepared through the condensation of a isophytol and trimethylhydroquinone (TMHQ) represented by the following reaction formula 1:

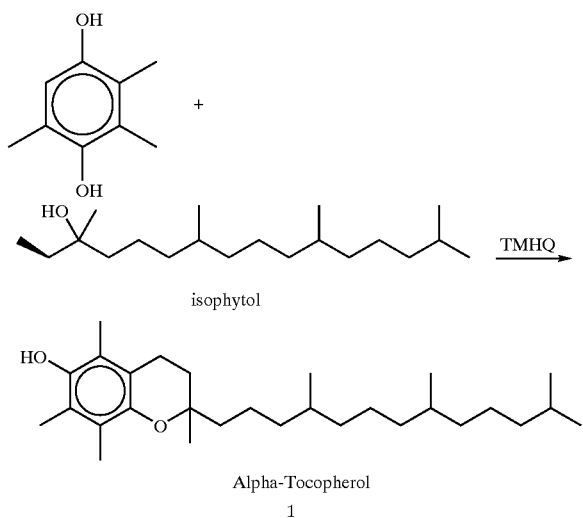

For example, U.S. Pat. No. 4,217,285 (hereinafter referred to as '285 patent), which is assigned to Nisshin, discloses the synthesis of DL-α-tocopherol in toluene or n-hexane solvent with $ZnCl_2$ and silica-alumina (or silica-gel) in the presence of acid, especially HCl, asserting that tocopherol can be obtained with a purity of 95 to 96% at a production yield of 99% or higher. Also, U.S. Pat. Nos. 4,634,781 and 4,639,533, both assigned to BASF, disclose processes for producing DL-α-tocopherol in which isophytol is reacted with amines such as tridecylamine or octadecylamine and thereafter with TMHQ in the presence of $ZnCl_2$ and HCl, which are somewhat complicated and inefficient. In those techniques, the tocopherol is described to be produced with a purity of 94 to 95% at a yield of 95 to 98%. Other preparation methods of DL-α-tocopherol can be found in U.S. Pat. Nos. 5,663,376 and 5,886,197, both assigned to Eisai Co., Ltd, in which isophytol is reacted with TMHQ in a mixed solvent system comprising a non-polar solvent and an alcohol or carbonate ester. It is described that DL-α-tocopherol can be produced at a yield of 94 to 98% with a purity of 92 to 97%.

However, the conventional techniques leave room for improving purity because their DL-α-tocopherol is as low as 95% on average purity. Particularly, the BASF and the Eisai patents are inefficient in that they do not satisfy the desired yield of DL-α-tocopherol. Such a disadvantage is attributed to the fact that, in the case that a Brönsted acid, such as hydrochloric acid, serving as a co-catalyst, is present from the early stage of the reaction, loss of the reactant isophytol occurs owing to the dehydration by the Brönsted acid, giving rise to a decrease in the total yield.

Being used as a solvent in the '285 patent, toluene or hexane brings about a poor total yield of DL-α-tocopherol. When used, toluene itself is partially reacted with isophytol to be produced undesired by-products. Hexane, although not reacting with isophytol, lengthens the reaction time owing to its low boiling point (approximately 69° C.) such that the catalyst induces the dehydration of isophytol. Furthermore, when the synthesis of DL-α-tocopherol is carried out under such a reaction procedure, by-products analogous in structure to DL-α-tocopherol are found in relatively large quantities, decreasing the purity of the DL-α-tocopherol separated. In addition, the total yield of DL-α-tocopherol is lowered when purifying it to a very high purity.

The '285 patent has an advantage over the above other patents in that it is high in the production yield of DL-α-tocopherol because of the use of silica gel or silica-alumina as a solid catalyst, however suffers from the disadvantage of being unable to recycle the silica catalyst because of the adsorptivity of silica for certain organic materials. For instance, in the case that the reactant TMHQ, reaction intermediates (the condensation may provide two intermediates owing to the reaction mechanism), and the required product DL-α-tocopherol are adsorbed onto the surface of the silica gel catalyst to prevent active functional sites of the catalyst such that the activity of the catalyst drops sharply. That is, it is impossible to reuse the silica gel catalyst. Furthermore, when the DL-α-tocopherol adsorbed onto the surface of the silica gel is not recovered, the total yield of DL-α-tocopherol becomes poor.

Another problem with the '285 patent resides in the existence of hydrochloric acid from the early stage of the reaction. As aforementioned, hydrochloric acid decomposes isophytol through dehydration to decrease the total yield, as well as causes other side-reactions which may occur between isophytol and TMHQ, to generate by-products which are similar in molecular weight to vitamin E, thereby lowering the purity thereof.

SUMMARY OF THE INVENTION

Knowledge of a catalytic reaction allows modification and adaptation leading to the present invention.

The intensive and extensive research on the preparation of DL-α-tocopherol from isophytol or phytol derivatives and TMHQ, conducted by the present inventors, resulted in the finding the preparation method of DL-α-tocopherol capable of minimizing the self-decomposition of isophytol or phytol derivatives and the generation of by-products by employing $MX_2$ as a main catalyst and silica gel and/or silica-alumina as a co-catalyst to form intermediates in the reaction mixture and thereafter adding a Brönsted acid as an additional catalyst to the reaction for obtaining a final product when the intermediates formation has been completed.

Therefore, it is an object of the present invention to provide a method for preparing DL-α-tocopherol with a high purity at a high yield.

It is another object of the present invention to provide a method for preparing DL-α-tocopherol from a minimum amount of isophytol or phytol derivatives relatively while generating substantially no by-products, whereby a great economical benefit can be brought about in terms of production cost.

It is a further object of the present invention to provide a method for preparing DL-α-tocopherol by use of a catalyst system which is highly effective even for application on a commercial scale and can be regenerated continually.

In accordance with the present invention, the above objects could be accomplished by a provision of a method for preparing DL-α-tocopherol with a high purity at a high yield, comprising:

a) adding isophytol or phytol derivatives to trimethylhydroquinone for the condensation thereof at 80 to 135° C. over 30 to 60 min in the presence of a catalyst system comprising main catalyst component and a co-catalyst in a reaction solvent to form intermediates, said main catalyst consisting of a divalent metal halogen compound represented by $MX_2$ wherein M is $Zn^{2+}$, $Fe^{2+}$ or $Sn^{2+}$ and X is F, Cl or I, said co-catalyst consisting of silica gel and/or silica-alumina;

b) adding a Brönsted acid to the resultant mixture of said a) step, thereafter to obtain a product through the separation; and c) washing the remaining co-catalyst with a polar solvent for recovery after said b) step, whereby the recovered co-catalyst can be reused for the preparation of DL-α-tocopherol.

DETAILED DESCRIPTION OF THE INVENTION

In accordance with the present invention, DL-α-tocopherol is prepared through the condensation between isophytol or phytol derivatives and TMHQ in the presence of a catalyst system comprising a main catalyst, a co-catalyst and an additional catalyst in a solvent selected from the group consisting of aliphatic saturated hydrocarbons, aromatic hydrocarbons, appropriate polar solvents and mixtures thereof. The main catalyst is represented by the general formula $MX_2$ wherein M is a divalent metal ion such as $Zn^{2+}$, $Fe^{2+}$ or $Sn^{2+}$ and X represents halogen such as F, Cl, Br or I. The co-catalyst is silica and/or silica-alumina while the additional catalyst is Brönsted acid, especially an aqueous HCl solution.

To achieve the present invention, various experiments for preparing DL-α-tocopherol through the condensation between isophytol or phytol derivatives and TMHQ were carried out with catalyst systems of $MX_2$ and various co-catalysts, which led to the finding that the starting materials go through intermediates to the final product via two sequential reaction steps. In the procedure, $MX_2$, serving as a main catalyst, mainly makes a contribution to the formation of intermediates while co-catalysts act to inhibit side-reactions as well as play a role in converting intermediates into DL-α-tocopherol in cooperation with the $MX_2$ catalyst. Silica (and/or silica-alumina) was identified as being a co-catalyst suitable for inhibiting side-reactions. However, once used, the silica gel catalyst could not be reused because unreacted TMHQ, decomposed isophytol or phytol derivatives, intermediates, and/or DL-α-tocopherol were adsorbed onto the surface of the silica gel to block the catalytically functional sites thereof.

On the other hand, where $ZnX_2$, silica gel and HCl are used simultaneously as in the '285 patent, the total amount of the substances adsorbed onto the silica gel is small as compared with when HCl is absent, but large as compared with the present invention comprising a washing procedure. What is worse, because isophytol or phytol derivatives are added in the presence of HCl from the beginning of the reaction, a relatively large quantity of the reactant is decomposed by itself, which leads to a decrease in the total yield. In addition, HCl causes side reactions between isophytol or phytol derivatives and TMHQ, lowering the purity of DL-α-tocopherol. Improved as it is, the regeneration of the silica gel in the conventional catalyst system is limited to several rounds.

Based on the finding that the catalytic role of $MX_2$ resides mainly in the formation of intermediates from the starting materials isophytol or phytol derivatives and TMHQ while the co-catalysts are chiefly responsible for the conversion of the intermediates into DL-α-tocopherol, the present inventors developed the conventional catalyst system to a more effective one which can prepare DL-α-tocopherol from a minimum amount of isophytol or phytol derivatives relatively while generating substantially no by-products. In addition, silica gel and/or silica-alumina used as a co-catalyst can be regenerated continually at least 20 times.

In this development, account was also sufficiently taken of the finding that side-reactions readily occur in the first or the second step for intermediate production from isophytol or phytol derivatives and TMHQ.

According to the present invention, the preparation of DL-α-tocopherol starts with the slow reaction of isophytol or phytol derivatives with TMHQ in the presence of an $MX_2$ catalyst and silica gel (and/or silica-alumina) in an appropriate solvent. For the slow reaction, isophytol or phytol derivatives are slowly added through, for example, a dropping funnel into the solvent containing TMHQ, the $MX_2$ catalyst and silica gel. Within 10 to 30 min after completion of the addition, most of the isophytol or phytol derivatives are reacted with TMHQ to form intermediates. Then, a Brönsted acid is added into the reactor. The Brönsted acid not only acts to react the isophytol or phytol derivatives, which remains unreacted at a trace amount, with TMHQ to form intermediates but also accelerates the formation of DL-α-tocopherol from the intermediates. In addition, the Brönsted acid assists to desorb the adsorbed substances, including TMHQ, self-decomposed isophytol or phytol derivatives, some by-products, intermediates, and DL-α-tocopherol, from the surface of the silica gel (and/or silica-alumina) to regenerate the activity of the silica gel (and/or silica-alumina) and plays a catalytic role in converting the desorbed intermediates into the final product in cooperation with the $MX_2$ and silica gel (and/or silica-alumina). Thus, the Brönsted acid makes a significant contribution to both the regeneration of the silica catalyst and the increase of the production yield.

Another advantage of adding the Brönsted acid after formation of intermediates is that the decomposition of isophytol or phytol derivatives can be effectively prevented in the early stage of the reaction. In addition to this suppressing effect, the Brönsted acid plays a catalytic role in converting the isophytol or phytol derivatives remaining unreacted and TMHQ, thereby enabling the improvement in the production yield. After completion of the reaction, products are isolated from the reaction. The remaining silica gel (and/or silica-alumina) catalyst is washed with a polar solvent in order to dissolve the TMHQ and DL-α-tocopherol adsorbed onto the surface of the silica gel (and/or silica-alumina), thus regenerating the silica gel (and/or silica-alumina) and increasing the production yield.

Suitable for use in the present invention is the Brönsted acid selected from the group consisting of hydrogen chloride gas, aqueous hydrochloric acid solutions, phosphoric acid, sulfuric acid, nitric acid, p-toluenesulfonic acid, and mixtures thereof, and the isophytol or phytol derivatives represented by the following chemical formulas I and II:

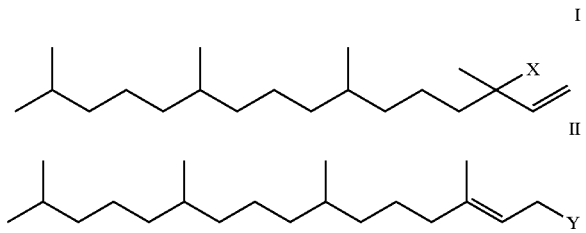

wherein X and Y are independently a hydroxy group, a halogen atom or an acetoxy group.

A comparison was made for the preparation of DL-α-tocopherol from isophytol or phytol derivatives and TMHQ through condensation among when a conventional catalyst system comprising $MX_2$, silical gel (and/or silica-alumina) and a Brönsted acid are used in one stage, when only $MX_2$ and silica gel (and/or silica-alumina) catalysts are used without a Brönsted catalyst, and when $MX_2$ and silica gel (and/or silica-alumina) are used to form the intermediates, followed by the addition of the Brönsted acid in accordance with the present invention. The results demonstrated that the present invention was superior in the production yield and purity of DL-α-tocopherol to the other preparation techniques.

A preferable preparation result is obtained when a catalyst combination of $MX_2$ and silica gel (and/or silica-alumina) according to the present invention is used at an amount of 5 to 300 weight parts based on 100 weight parts of TMHQ. The range of 20 to 150 weight parts of this catalyst combination brings about a more preferable result in the preparation of DL-α-tocopherol. DL-α-tocopherol is preferably prepared using $MX_2$ and silica gel (and/or silica-alumina) in the ratio of 1:0.5 to 1:5 and more preferably in the ratio of 1:0.7 to 1:2. In terms of the catalytically effective quantity, an excellent product of tocopherol is obtained when the amount of the catalyst is maintained in a specific range with respect to the amount of TMHQ. That is, when the relative ratio of $MX_2$ and silica gel (and/or silica-alumina) is maintained in such a range, an excellent result is achieved in the preparation of DL-α-tocopherol.

No specific limitations are imposed on the silica gel used in the present invention. Preferably, the silica gel has a BET surface area of 100 $m^2/g$ or greater and the silica-alumina has a BET surface area of 500 $m^2/g$ or greater. At the point of forming intermediates, a Brönsted acid is preferably introduced at an amount of 3 to 200 weight parts based on 100 weight parts and most preferably at an amount of 10 to 50 weight parts. When present at an amount within this range, the Brönsted acid inhibits side-reactions, improving the production yield of DL-α-tocopherol. Also, the Brönsted acid enables the catalyst to be regenerated.

In terms of the addition point of the Brönsted acid, most preferable results are obtained in the time range of from 3 to 60 min after the addition of isophytol or phytol derivatives to the reaction mixture. Particularly in terms of yield and purity, the most preferable addition point falls within the range of 5 to 20 min after the addition of isophytol or phytol derivatives. The yield and purity is not greatly deteriorated even at a late addition time, however the total reaction time is extended. Accordingly, it is preferable to add the Brönsted acid within two hours after the addition of isophytol or phytol derivatives.

Examples of the solvent useful in the present invention include aromatic hydrocarbons such as toluene, benzene and xylene and aliphatic saturated hydrocarbons such as n-heptane, mixed-heptane, n-hexane, mixed-hexane, n-octane, mixed-octane, n-decane and mixed-decane, and some polar solvents such as butylacetate, dichloroethane, dichloromethane, ethylacetate, methylacetate and diethylmalonate with a preference for toluene, n-heptane and mixed-heptane. Of them, n-heptane and mixed-heptane guarantee the most preferable synthesis results in the present invention. The polar solvent useful to wash the silica gel and/or silica-alumina catalyst is selected from the group consisting of methylacetate, ethylacetate (acetic acid ethyl), propylacetate, butylacetate, pentylacetate, acetone, methylethyl ketone, diethyl ketone, methylisopropyl ketone, methanol, ethoanol, propanol, isopropyl alcohol, butanol, pentanol, hexanol, heptanol, octanol and mixtures thereof.

A preferable period of reaction time (including the addition time of isophytol or phytol derivatives) is in the range of 2 to 7 hours and a more preferable period in the range of 2 to 3 hours, while suitable reaction temperatures fall within the range of 80 to 120° C.

In terms of yield, a preferable result is obtained when isophytol or phytol derivatives are added at an amount of 95 to 110 equivalents based on 100 equivalents of TMHQ. Particularly preferable results are obtained in the range of 100 to 105 equivalents of isophytol or phytol derivatives.

A better understanding of the present invention may be obtained in light of the following examples which are set forth to illustrate, but are not to be interpreted to limit the present invention.

Compatative Example 1

A 100 ml round-bottom flask equipped with a Dean-Stark device and a condenser was purged with nitrogen, after which 6.24 g (0.041 mole) of TMHQ, 4.16 g of silica gel and 2.08 g (0.015 mole) of $ZnCl_2$ were placed in the flask and added with 134 ml of n-heptane and the solution was stirred. The flask was equipped with a dropping funnel with nitrogen purging through the flask. A solution of 12.48 g (0.042 mole) of isophytol in 10 ml of n-heptane was placed in the dropping funnel and the flask was heated for refluxing under the nitrogen atmosphere. On refluxing, the solution of isophytol in n-heptane was slowly added through the dropping funnel into the flask over 1 hour. After completion of the addition, the reaction was further carried out under reflux for another 2 hours. The product mixture was analyzed by GC, and the conversion of TMHQ was found to be 96.9% and the purity of DL-α-tocopherol to be 99.1%.

Comparative Example 2

Under the same reaction conditions as in Comparative Example 1, 6.24 g (0.041 mole) of TMHQ, 4.16 g of silica gel, 2.08 g (0.015 mole) of $ZnCl_2$, and 2 g of a 37% HCl aqueous solution (HCl 0.019 mole) were placed in the flask and added with 134 ml of n-heptane, followed by stirring the resulting solution. Under reflux in the nitrogen atmosphere, 12.48 g (0.42 mole) of isophytol was slowly added in the same manner as in Comparative Example 1. After completion of the addition, the reaction was further carried out under reflux for another 1 hour. The product mixture was analyzed by GC, and the conversion of TMHQ was found to be 96% and the purity of the DL-α-tocopherol obtained to be 96.5%.

EXAMPLE 1

Under the same reaction conditions as in Comparative Example 1, 6.24 g (0.041 mole) of TMHQ, 4.16 g of silica gel, and 2.08 g (0.015 mole) of $ZnCl_2$ were placed in the flask and added with 134 ml of n-heptane, followed by stirring the resulting solution. Under reflux in a nitrogen atmosphere, 12.48 g (0.42 mole) of isophytol was slowly added over 1 hour in the same manner as in Comparative Example 1. 10 min after completion of the addition, 2 g of a 37% HCl aqueous solution (HCl 0.019 mole) was added thereto and the reaction was further carried out under reflux for another 50 min. The product mixture was analyzed by GC, and the conversion of TMHQ was found to be 99.4% and the purity of the DL-α-tocopherol obtained to be 99.1%.

EXAMPLE 2

Under the same reaction conditions as in Comparative Example 1, 6.24 g (0.041 mole) of TMHQ, 4.16 g of silica-alumina, and 2.08 g (0.015 mole) of $ZnCl_2$ were placed in the flask and added with 134 ml of n-heptane, followed by stirring the resulting solution. Under reflux in a nitrogen atmosphere, 12.48 g (0.42 mole) of isophytol was slowly added over 1 hour in the same manner as in Comparative Example 1. 10 min after completion of the addition, 2 g of a 37% HCl aqueous solution (HCl 0.019 mole) was added thereto and the reaction was further carried out under reflux for another 50 min. The product mixture was analyzed by GC, and the conversion of TMHQ was found to be 99.2% and the purity of the DL-α-tocopherol obtained to be 98.8%.

EXAMPLE 3

Under the same reaction conditions as in Comparative Example 1, 6.24 g (0.041 mole) of TMHQ, 4.16 g of silica gel, and 2.08 g (0.015 mole) of $ZnCl_2$ were placed in the flask and added with 134 ml of toluene, followed by stirring the resulting solution. Under reflux in a nitrogen atmosphere, 12.48 g (0.42 mole) of isophytol was slowly added over 1 hour in the same manner as in Comparative Example 1. 10 min after completion of the addition, 2 g of a 37% HCl aqueous solution (HCl 0.019 mole) was added thereto and the reaction was further carried out under reflux for another 50 min. The product mixture was analyzed by GC, and the conversion of TMHQ was found to be 96.5% and the purity of the DL-α-tocopherol obtained to be 99.1%.

The results obtained in above examples are summarized in Table 1, below.

Through the following examples, the ability of the present invention to regenerate silica gel and/or silica-alumina continually will be proven.

Comparative Example 3

Under the same reaction conditions as in Comparative Example 1, 6.24 g (0.041 mole) of TMHQ, 4.16 g of silica gel, and 2.08 g (0.015 mole) of $ZnCl_2$ were placed in the flask and added with 134 ml of n-heptane, followed by stirring the resulting solution. Under reflux in a nitrogen atmosphere, 12.48 g (0.42 mole) of isophytol was slowly added over 1 hour in the same manner as in Comparative Example 1. After completion of the addition, the reaction was further carried out under reflux for another 2 hours. Then, the product mixture was removed using a pump installed with a filter. The silica gel in the reactor was added with 50 ml of n-heptane, stirred for 5 min and filtered for recovery. Using this recovered silica gel, DL-α-tocopherol was synthesized as in the above. The same silica gel was reused for the same above preparation procedure 5 times in total. The product mixture was analyzed by GC for every round of the reaction. In the final round of the reuse, the conversion of TMHQ was found to be 82.4% and the purity of the DL-α-tocopherol obtained to be as low as 78.8%.

EXAMPLE 4

Under the same reaction conditions as in Comparative Example 3, 6.24 g (0.041 mole) of TMHQ, 4.16 g of silica gel, and 2.08 g (0.015 mole) of $ZnCl_2$ were placed in the flask and added with 134 ml of n-heptane, followed by stirring the resulting solution. Under reflux in a nitrogen atmosphere, 12.48 g (0.42 mole) of isophytol was slowly added over 1 hour in the same manner as in Comparative Example 1. 10 min after completion of the addition, 2 g of a 37% HCl aqueous solution (HCl 0.019 mole) was added thereto and the reaction was further carried out under reflux for another 50 min. Then, the product mixture was removed using a pump installed with a filter. The silica gel in the reactor was added with 50 ml of ethyl acetate, stirred for 5 min and filtered for recovery. Using this recovered silica gel, DL-α-tocopherol was prepared as in the above. The same silica gel was reused for the same above preparation procedure 20 times in total. The product mixture was analyzed by GC for every round of the reaction. In the final round of the reuse, the conversion of TMHQ was found to be 98.7% and the purity of the DL-α-tocopherol obtained to be as high as 99.0%.

Quantitative results of Example 4 are given, along with those of Comparative Example 3, in Table 2, below.

TABLE 1

| Example No. | Catalyst | Solvent | Rxn Temp (° C.) | Rxn Time (hr) | Yield (%) | Purity (%) |
|---|---|---|---|---|---|---|
| C. Exmp 1 | $ZnCl_2/SiO_2$ gel | n-heptane | 95 | 3 | 96.9 | 99.1 |
| C. Exmp 2 | $ZnCl_2/SiO_2$ gel/HCl | n-heptane | 95 | 2 | 96.0 | 96.5 |
| Exmp 1 | $ZnCl_2/SiO_2$ & HCl (add later) | n-heptane | 95 | 2 | 99.4 | 99.1 |
| Exmp 2 | $ZnCl_2/SiO_2$—$AlO_3$ & HCl (add later) | n-heptane | 95 | 2 | 99.2 | 98.8 |
| Exmp 3 | $ZnCl_2/SiO_2$ & HCl (add later) | toluene | 110 | 2 | 96.5 | 99.1 |

TABLE 2

| Recycling Round | C. Example 3 ZnCl$_2$/Silica Gel/ n-Heptane | | Example 4 ZnCl$_2$/Silica Gel/HCl (add later)/n-Heptane | |
|---|---|---|---|---|
| | Yield (%) | Purity (%) | Yield (%) | Purity (%) |
| 1 | 96.9 | 99.1 | 99.4 | 99.1 |
| 2 | 94.2 | 98.6 | 98.8 | 98.9 |
| 3 | 92.1 | 96.2 | 99.0 | 99.1 |
| 4 | 90.5 | 88.3 | 99.4 | 99.2 |
| 5 | 82.4 | 78.8 | 98.8 | 98.8 |
| 6 | — | — | 99.0 | 99.2 |
| 8 | | | 98.6 | 98.8 |
| 10 | | | 98.4 | 98.9 |
| 15 | | | 98.5 | 98.8 |
| 20 | | | 98.7 | 99.0 |

From isophytol and TMHQ, as described hereinbefore, intermediates are formed as a result of the catalytic action of the combined catalyst system comprising MX$_2$ and silica gel (and/or silica-alumina) and converted into DL-α-tocopherol under the catalytic influence of the combined catalyst system in cooperation with a Brönsted acid. The catalyst system according to the present invention can remarkably reduce side-reactions upon the condensation between isophytol and TMHQ in comparison with the conventional catalysts for use in preparing DL-α-tocopherol; thus producing DL-α-tocopherol with a high purity at a high yield. In addition, over the conventional catalyst systems, the catalyst system according to the present invention has the advantage of being reusable in succession because of its being able to avoid the decrease of catalytic activity attributed to the adsorption of organic materials; thus reducing the production cost of DL-α-tocopherol and the quantity of industrial wastes generated. With these advantages, the catalyst system according to the present invention can be effectively used in preparing highly pure DL-α-tocopherol at a high yield on a commercial scale.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A method for preparing DL-α-tocopherol with high purity at a high yield, comprising:
   a) adding isophytol or phytol derivatives represented by Formula I or II,

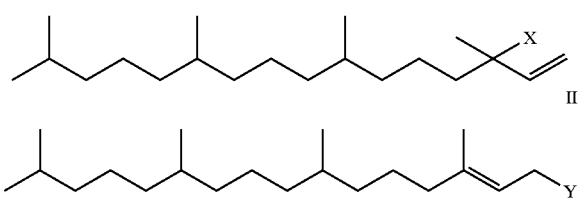

wherein X and Y are independently a hydroxy group, a halogen atom or an acetoxy group, to trimethylhydroquinone for the condensation thereof at 80 to 135° C. over 30 to 60 min in the presence of a catalyst system comprising a main catalyst component and a co-catalyst in a reaction solvent to form intermediates, said main catalyst consisting of a divalent metal halogen compound represented by MX$_2$ wherein M is Zn$^{2+}$, Fe$^{2+}$ or Sn$^{2+}$ and X is F, Cl or I, said co-catalyst consisting of silica gel and/or silica-alumina;
   b) adding a Brönsted acid to the resultant mixture of said step a) to thereafter obtain DL-α-tocopherol by separation; and
   c) recovering the remaining co-catalyst by washing with a polar solvent after said step b), whereby the recovered co-catalyst can be reused for the preparation of DL-α-tocopherol.

2. The method as set forth in claim 1, wherein the reaction solvent is selected from the group consisting of aliphatic saturated hydrocarbon, aromatic hydrocarbon, polar solvent and mixtures thereof.

3. The method as set forth in claim 2, wherein the aromatic hydrocarbon is toluene, benzene or xylene, the aliphatic saturated hydrocarbon is n-heptane, mixed-heptane, n-hexane, mixed-hexane, n-octane, mixed-octane, n-decane or mixed-decane, and the polar solvent is butylacetate, dichloroethane, dichloromethane, ethylacetate, methylacetate or diethylmalonate.

4. The method as set forth in claim 1, wherein the Brönsted acid is selected from the group consisting of hydrochloric acid, aqueous hydrochloric acid solutions, phosphoric acid, sulfuric acid, nitric acid, p-toluenesulfonic acid, and mixtures thereof.

5. The method as set forth in claim 1, wherein the polar solvent is selected from the group consisting of methylacetate, ethylacetate, propylacetate, butylacetate, pentylacetate, acetone, methylethyl ketone, diethyl ketone, methylisopropyl ketone, methanol, ethoanol, propanol, isopropyl alcohol, butanol, pentanol, hexanol, heptanol, octanol and mixtures thereof.

6. The method as set forth in claim 1, wherein the catalyst system comprising MX$_2$ and silica gel and/or silica alumina is used at an amount of 5 to 300 weight parts based on 100 weight parts of trimethylhydroquinone.

7. The method as set forth in claim 1, wherein the catalyst system comprising MX$_2$ and silica gel and/or silica alumina is used at an amount of 20 to 150 weight parts based on 100 weight parts of trimethylhydroquinone.

8. The method as set forth in claim 1, wherein the silica gel and/or silica-alumina is used at an amount of 50 to 500 weight parts based on 100 weight parts of MX$_2$.

9. The method as set forth in claim 1, wherein the silica gel and/or silica-alumina is used at an amount of 70 to 200 weight parts based on 100 weight parts of MX$_2$.

10. The method as set forth in claim 1, wherein the silica gel has a BET (Brauner, Emmel & Teller) surface area of 100 m$^2$/g or greater and the silica-alumina has a BET surface area of 500 m$^2$/g or greater.

11. The method as set forth in claim 1, wherein the Brönsted acid is added within 2 hours after the addition of the isophytol or phytol derivatives.

12. The method as set forth in claim 1, wherein the Brönsted acid is used at an amount of 3 to 200 weight parts based on 100 weight parts of trimethylhydroquinone.

13. The method as set forth in claim 1, wherein the Brönsted acid is used at an amount of 10 to 50 weight parts based on 100 weight parts of trimethylhydroquinone.

14. The method as set forth in claim 1, wherein the isophytol or phytol derivatives are used at an amount of 95 to 110 equivalents based on 100 equivalents of trimethylhydroquinone.

15. The method as set forth in claim 14, wherein the isophytol or phytol derivatives are used at an amount of 100 to 105 equivalents based on 100 equivalents of trimethylhydroquinone.

* * * * *